(12) United States Patent
Laitio et al.

(10) Patent No.: US 7,231,244 B2
(45) Date of Patent: Jun. 12, 2007

(54) METHOD AND ARRANGEMENT FOR PREDICTING PERIOPERATIVE MYOCARDIAL ISCHEMIA

(75) Inventors: Timo Laitio, Turku (FI); Heikki Huikuri, Oulu (FI); Jouko Jalonen, Turku (FI); Erkki Kentala, Turku (FI); Harry Scheinin, Piispanristi (FI)

(73) Assignee: GE Healthcare Finland Oy, Helsinki (FI)

( * ) Notice: Subject to any disclaimer, the term of this patent is extended or adjusted under 35 U.S.C. 154(b) by 0 days.

(21) Appl. No.: 10/740,369

(22) Filed: Dec. 18, 2003

(65) Prior Publication Data

US 2005/0137482 A1 Jun. 23, 2005

(51) Int. Cl.
*A61B 5/04* (2006.01)

(52) U.S. Cl. ............... 600/509; 600/519; 600/515; 607/9

(58) Field of Classification Search .......... 600/515, 600/509, 519; 607/9
See application file for complete search history.

(56) References Cited

U.S. PATENT DOCUMENTS

| | | | | |
|---|---|---|---|---|
| 3,755,783 | A * | 8/1973 | Astarjian et al. | 600/515 |
| 5,201,321 | A * | 4/1993 | Fulton | 600/515 |
| 6,559,128 | B1 | 5/2003 | Hamm et al. | |
| 2003/0096297 | A1 | 5/2003 | Gilchrist et al. | |
| 2004/0018558 | A1 | 1/2004 | Gilchrist et al. | |

OTHER PUBLICATIONS

Correlation between preoperative ischemia and major cardiac events after peripheral vascular surgery, K.E. Raby, et al., N Engl J Med. Nov. 9, 1989;321(19):1296-300.*

The ability of several short-term measures of RR variability to predict mortality after myocardial infarction, J.T. Bigger, et al., Circulation. Sep. 1993;88(3):927-34. □□*

Skinner et al. "Correlation dimension of heartbeat intervals is reduced in conscious pigs by Myocardial Ischemia." Circulation Research Apr. 1991; 68(4): 966-76.*

Fractal dynamics in physiology: Alterations with disease and aging, Ary L. Goldberger, et al., PNAS, Feb. 19, 2002, vol. 99, Suppl. 1, pp. 2466-2472.

Epidural infusion of bupivacaine and fentanyl reduces perioperative myocardial ischaemia in elderly patients with hip fracture—a randomized controlled trial, H. Scheinin, et al., Acta Anaesthesiologica Scandinavica, ISSN 0001-5172, pp. 1061-1070, no date.

Detrended fluctuation analysis, Ary L. Goldberger et al., www.phsionet.org., 2000.

(Continued)

*Primary Examiner*—Robert Pezzuto
*Assistant Examiner*—Shevon Johnson
(74) *Attorney, Agent, or Firm*—Andrus, Sceales, Starke & Sawall, LLP (57) ABSTRACT

A method and an arrangement for predicting perioperative myocardial ischemia. Heart rate measurements are carried out for example at night- and day-time before the operation to obtain heart rate data. The heart rate data obtained is carried to a device configured to carry out heart rate variability analysis (HRV). Dynamic heart rate variability analysis is carried out by utilizing fractal analysis of the heart rate data and fractal correlation properties obtained from the measured heart rate data are examined to find considerable lowering of the fractal correlation properties during for example night-time when compared to day-time.

34 Claims, 3 Drawing Sheets

OTHER PUBLICATIONS

Fractal Mechanisms in Neural Control: Human Heartbeat and Galt Dynamics in Health and Disease; Golderberg et al., www.physionet.org.

*Atrial Fibrillation after Coronary Artery Bypass Surgery, A Study of Causes and Risk Factors*, Lena Jidéus, Comprehensive Summaries of Uppsala Dissertations from the Faculty of Medicine 1093, Acta Universitatis Upsaliensis Uppsala 2001.

Dyer et al., Molecular and Biochemical Parasitology 110, 437-448 (2000).

Harrison, et al., Science 301, 1734-1736 (2003).

Thélu, et al., Cellular Signaling 6, 777-782 (1994).

Taraschi, et al., *Blood*, 102, 3420-3426 (2003).

Lauer, et al., *The EMBO Journal*, 19, 3556-3564 (2000).

Samuel, et al., *Journal of Biological Chemistry*, 276, 29319-29329 (2001).

Gilchrist, et al., *Journal of Biological Chemistry*, 273, 14912-14919 (1998).

Gilchrist, et al., *Journal of Biological Chemistry*, 274, 6610-6616 (1999).

Vanhauwe, et al., *Journal of Biological Chemistry*, 277, 34143-34149 (2002).

Etienne-Manneville, et al., *Nature*, 420, 629-635 (2002).

Gardner et al., *Nature*, 419, 498-511 (2002).

Brittain, et al., *Journal of Clinical Investigation*, 107, 1555-1562 (2001).

Green, et al., *Journal of Cell Biology*, 146, 673-682 (1999).

\* cited by examiner

METHOD AND ARRANGEMENT FOR PREDICTING PERIOPERATIVE MYOCARDIAL ISCHEMIA

BACKGROUND OF THE INVENTION

The invention relates to a method and arrangement for predicting perioperative myocardial ischemia.

Patients with myocardial ischemia after non-vascular and non-cardiac vascular surgery have 3 to 9-fold risk of adverse cardiac events, respectively, and cardiac complications account for more than half of the deaths. Especially prolonged ischemia over 10 minutes has been recently shown to be a strong predictor for postoperative death and myocardial infarction. The prevalence of perioperative myocardial Ischemia in unselected hip fracture patients has been reported to be over 30%. The term perioperative refers to time before the operation, under the operation and after the operation. Complications are mainly due to ischemic events, pneumonia and lung embolism. The 3-year mortality rate is over 30%, and almost half of those who survive are permanently institutionalized.

The autonomic nervous system plays a significant role in the pathophysiology of perioperative ischemia. There is evidence that sympathetic activation has an important role in the onset of adverse cardiac events. Adrenergic activity and plasma catecholamine levels change considerably in the postoperative period, which may predispose to myocardial ischemia by altering relationship between myocardial oxygen demand and supply. Furthermore, increased sympathetic activation during REM sleep has been suggested to be associated with the circadian pattern of ischemia occurring most frequently during early morning hours.

Heart rate variability (HRV) measures from ambulatory electrocardiograph recordings are widely used in the assessment of cardiovascular autonomic regulation. Recent studies suggest that newer measures of HRV, such as fractal analysis methods can complement the traditional time and frequency domain HRV measures in risk stratification of patients with heart disease. These new dynamic analysis methods describe qualitative rather than quantitative properties of HRV. Fractal correlation properties exhibit long-range correlations between RR-intervals; i.e., interbeat interval at every time point is partially dependent on the intervals at all previous time points. An article "Fractal dynamics in physiology: Alterations with disease and aging" Goldberger et al, Feb. 19, 2002, can be mentioned as an example of the prior art.

The American Heart Association has issued guidelines to identify patients at greater risk for postoperative adverse cardiac outcome preoperatively but diagnostic tools with better performance in risk stratification are still needed.

SUMMARY OF THE INVENTION

The object of the invention is to obtain an effective tool to predict perioperative myocardial ischemia. This is achieved by the invention. The method according to the invention is characterized by the steps:

carrying out heart rate measurements at night- and day-time before the operation to obtain preoperative heart rate data for night and day, transferring the heart rate data obtained to a device configured to carry out heart rate variability analysis (HRV), and carrying out dynamic heart rate variability measures by utilizing fractal analysis from the heart rate data obtained and comparing fractal correlation properties obtained from the preoperative heart rate date measured for night and day to see if the fractal correlation properties were significantly lower during the night-time compared with day-time.

The method according to the invention is also characterized by the steps:

carrying out heart rate measurements perioperatively to obtain heart rate data, transferring the heart rate data obtained to a device configured to carry out heart rate variability analysis (HRV), and carrying out dynamic heart rate variability measures by utilizing fractal analysis from the heart rate data obtained and comparing fractal correlation properties obtained from the heart rate data measured to find considerable lowering of the fractal correlation properties before ischemia.

The arrangement according to the invention comprises:

means configured to carry out heart rate measurements at night- and day-time before the operation to obtain preoperative heart rate data for night and day, means configured to carry out heart rate variability analysis (HRV), means configured to transfer the heart rate data obtained to the means configured to carry out heart rate variability analysis (HRV), and means configured to carry out dynamic heart rate variability measures by utilizing fractal analysis from the heart rate data obtained and to compare fractal correlation properties obtained from the preoperative heart rate data measured for night and day to see if the fractal correlation properties were significantly lower during the night-time compared with day-time.

The other embodiment of the invention comprises:

means configured to carry out heart rate measurements perioperatively to obtain heart rate data, means configured to carry out heart rate variability analysis (HRV), means configured to transfer the heart rate data obtained to the means configured to carry out heart rate variability analysis (HRV), means configured to carry out dynamic heart rate variability measures by utilizing fractal analysis from the heart rate data obtained and to compare fractal correlation properties obtained from the heart rate data measured to find considerable lowering of the fractal correlation properties before ischemia.

BRIEF DESCRIPTION OF THE DRAWINGS

In the following the invention will be described in more detail by means of the study carried out and the drawing enclosed in which.

DETAIL DESCRIPTION OF THE INVENTION

The study was carried out at Turku University Hospital in Finland. Thirty-two patients, age 60 or older, admitted to hospital for surgical repair of a traumatic hip fracture with preoperative night- and day-time Holter recordings were included in this study. The patients were from the earlier study published in 2000, "Epidural infusion and fentanyl reduces perioperative myocardial ischemia in elderly patients with hip fracture", Scheinin H, Virtanen T, Kentala E, et al, Acta Anaesthesiol Scand 2000;44:1061–70, which evaluated the incidence of perioperative ischemia in 59 traumatic hip fracture patents treated with continuous epidural infusion or conventional parenteral opiates. Twenty-seven patients, not included in the present study, were operated soon after hospital intake, and therefore had no preoperate night and day ECG recordings. Patients with other than sinus rhythm or with significant conduction abnormalities were excluded. All patients were operated under spinal anesthesia. Cardiac medications (excluding diuretics) were continued normally throughout the study period.

Figure 1:
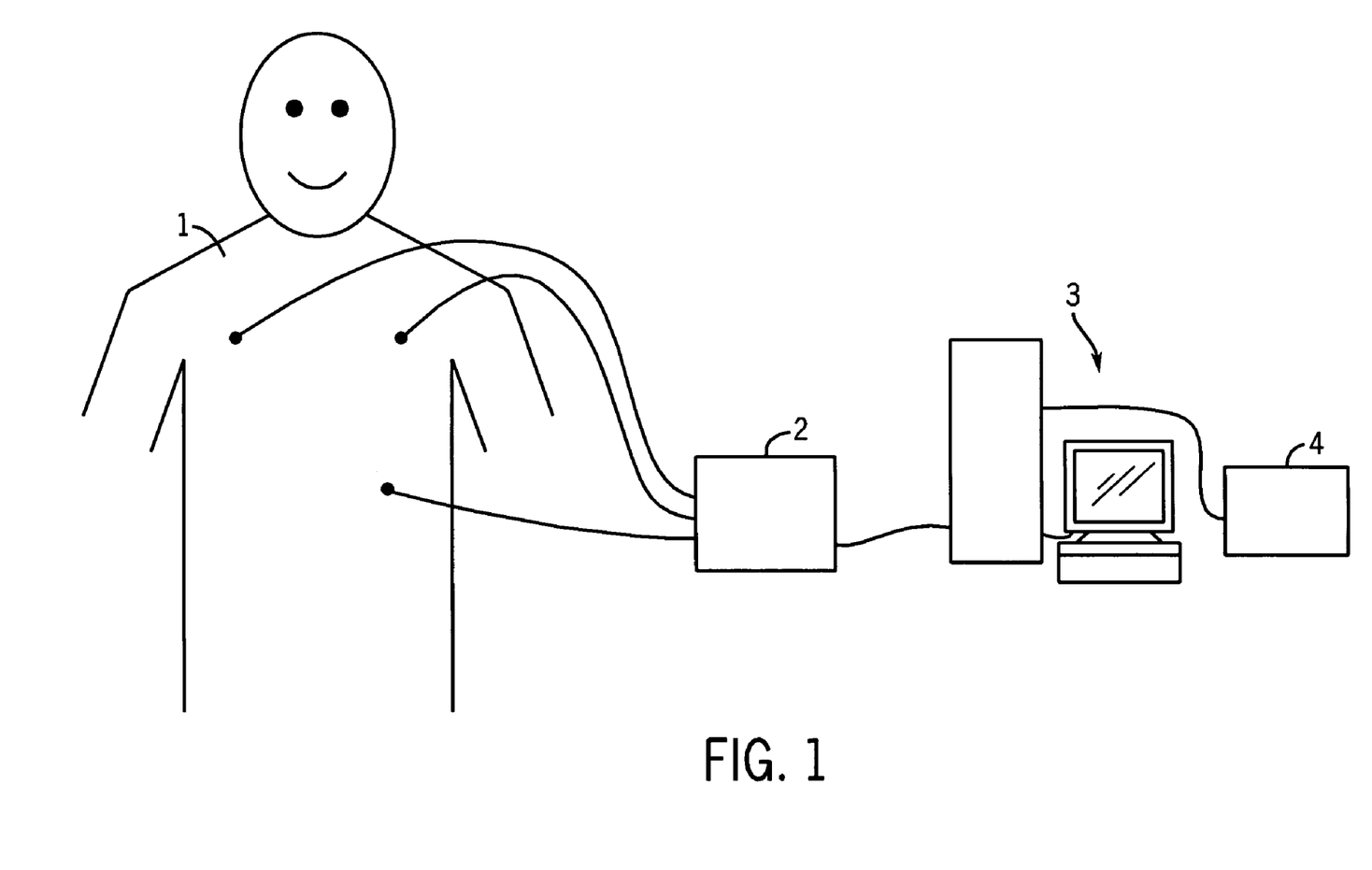
FIG. 1 shows a schematic view of the arrangement used in the invention.

FIG. 1 is a schematic view of th arrangement,used in the invention. FIG. 1 shows a patient 1. Heart rate data were obtained from the patient with two channel Holter recording with an analog device. ECG Hoater data were sampled digitally by using a scanner device 2 and then transferred to a computer 3 for further analysis as described later. A printer is described with a reference number 4 in FIG. 1.

Preoperative two channel continuous Holter recording with an analog device with temporal resolution of 128 Hz (Marquette Electronics Inc., series 8500, Milwaukee, Wis., USA) was initiated immediately after recruitment and continued until the third postoperative morning. Two bipolar leads were used: a modified V5 lead ($5^{th}$ intercostals space at the left mid-clavicular line). The corresponding reference electrodes were in the right and left first intercostals space at the mid-clavicular lines. A horizontal or down-sloping ST-segment depression $\geq 1.0$ mm (0.1 mV) or an elevation $\geq 2.0$ mm (0.2 mV) at 0.06 sec after the J-point with over 10 minute duration in Holter data were defined as reversible prolonged ischemic changes. All data was also analyzed with short ischemic episodes of at least 1 minute. For each ischemic episode the maximum ST-deviation, its duration, and the area under the ST deviation×time curve (AUC) were determined. The ECG Holter data were sampled digitally and the transferred from the scanner (Oxford Medical Ltd.) to a computer for further analysis of HRV. A careful manual editing of the RR-interval series with inspection of the ECG data by deleting premature beats and noise were performed. All RR-intervals of suspected portions were printed-out on a 2-channel ECG at a paper speed of 25 mm/sec to confirm the sinus origin of all RR-interval data.

Heart rate and standard deviation of all RR-intervals (SDNN) of 24 hour data were used as conventional indices of HRV. An autoregressive modeling with a model order 20 was used to estimate power spectral densities of RR-interval time series. The power spectra were quantified by measuring the areas in the following frequency bands: very low frequency (VLF) power (0.0033–0.04 Hz), low frequency (LF) power (0.04–0.15 Hz), and high frequency (HF) power. Detrended fluctuation analysis (DFA) was used to quantify fractal-like scaling properties of the time series. Detrended fluctuation analysis is described In www.physionet.org. and also Goldberger A L, Amaral L A, Glass L, Hausdorff J M, lvanov P C, Mark R G, Mietus J E, Moody G B, Peng C K, Stanley H E (2000). Physiobank, PysioToolkit, and PhysioNet: components of a new research resource for complex physiologic signals. Circulation 101:E215–220. Shortly, the deviations of each RR intervals from the average RR-interval are Integrated over the selected window (1000 beats). Then the window is divided into smaller windows (time scales) and at least squares line fit is applied to the data in each window. This produces a "local" trend which is subtracted from the overall integrated time series, producing detrended time series. Then a root mean square fluctuation from this integrated and detrended time series is repeatedly calculated using different time scales. Typically, there is a linear relationship between the logarithm of the fluctuation and the logarithm of the size of the time scale. The scaling exponent represents the slope of this line, which relates (log)fluctuation to log(window) size. The present heart rate correlation was defined for short-term fractal-like correlation $\alpha 1$ (window size $\leq 11$ beats) of RR-interval data, based on a previous finding of altered short-term heart rate behavior among elderly subjects. An exponent value of 0.5 means that there are no correlations between the RR-intervals as a result of random heart rate dynamics. An exponent value of 1.0 contains both random and highly correlated characteristics In RR-interval time series and has been interpreted to indicate fractal heart dynamics, and has been documented for healthy heart rate dynamics.

Referring to the matters described above it can be said that the fluctuation of the time series in a certain window size is plotted in the function of the window size in a log-log scale. In the case of short-term fractal scaling exponent, the window size is small (e.g. less than 12 beats, the number of beats can be agreed according to the existing need for example). Few window sizes can be used (e.g. 5) and the fluctuation increase as the window size increases in a linear fashion within small window sizes. Finally, the slope of this linear line is calculated. The slope is termed as short-term fractal scaling exponent $\alpha 1$ because in this case the small window sizes were used. Short-term fractal scaling exponent $\alpha 1$ of the DFA method quantifies the fractal-like correlation properties of short-term (for example $\leq 11$ beats) RR-interval data.

All preoperative ECG data with ischemic ST-segment changes were excluded from the HRV analysis. Association of the preoperative HRV measures and the postoperative ischemia were analyzed. Mean values of the LIRV parameters for preoperative RR-intervals as a whole epoch (i.e. $\geq 16$ hours of data prior surgery), and night (from 2 am to 5 am) and day (7 am to 12 am, all patients were awakened at 7 am) periods were calculated as an average of 1000 beat segments for each patient. The night-day differences was also calculated (i.e. the night value minus the day value). The period of night-time was selected based on earlier findings that the majority of REM sleep occur during late night between 2 am and 5 am.

Occurrence of at least one prolonged (over 10 min) postoperative ischemic episode was used as the criterion for division of the patients into two groups. The comparisons of the ischemia and the non-ischemia groups in patient characteristics were carried out using the Fisher's exact test or the two-sample t-test. Associations of different HRV measures with postoperative ischemia were tested using univariate logistic regression model. The predictive value of preoperative HRV measures for postoperative ischemia was also tested with multivariate analyses, First, all preoperative HRV measures were included in a stepwise multivariate logistic regression analysis. Statistically significant predictors were then included in further multivariate analyses including other potential explanatory factors divided into several subgroups, i.e. demographic factors, concomitant diseases and concomitant medications, clinical variables listed in table 1, analgesic regimen and quality of sleep and pain scores (using visual analogue scale). Because of the small sample size, the significance for the final model was confirmed using exact techniques in calculations. The results were quatified with odd ratios (OR) and 95% confidence intervals (CI). The Ors were calculated corresponding to a change equal to interquartile range in the predictor variable.

The goodness of fit of the final model was tested using Hoamer and Lemeshow Goodness-of-Fit test. The area under the receiver operating characteristic (ROC) curve (c-index) was calculated as the criterion for sensitivity of the final logistic model. The SAS System for Windows, release 8.2/2001 was used in the calculations A p-value of 0.05 was used as the threshold for significance.

One patient was excluded due to a continuous ischemia and three patients due to technical recording problems. Thus 28 patients were included in the final analysis. There were 16 patients without perioperative prolonged ischemia, and 12 patients with postoperative prolonged ischemia. Five patients han preoperative ischemia and all of them had also postoperative ischemia. Patient characteristics and details of ischemia are shown in tables 1 and 2.

The preoperative values of average of 24 hour time and frequency domain and $\alpha 1$ measure were not found to be associated with ischemia. Pre-operative $\alpha 1$ was significantly lower during the night-time compared with day-time (mean±SEM; 0.92±0.08 vs. 1.03±0.06, p=0.002, table 3) in patients with postoperative prolonged myocardial ischemia and the night-day difference of $\alpha 1$ was significantly associated with postoperative ischemia. Time and frequency domain measures did not show any significant association with ischemia.

In stepwise multivariate logistic regression analysis including the recorded risk factors for postoperative ischemia, increased preoperative night-day difference of scaling exponent $\alpha 1$ was the only independent predictor of prolonged postoperative ischemia. The goodness of fit test of the model indicated a good fit (p=0.163). The OR for an increase of 0.16 units in night-day difference of $\alpha 1$ (corresponding to interquartile range) was 7.7; 95% confidence interval (CI): 1.9–51.4; p=0.0018. The respective values for all ischemia in 13 patients (one patient had one short ischemic episode of 1.7 minutes) were as follows: OR 11.7; 95% CI:2.3–108.5; p<0.001.

Scaling exponent $\alpha 1$ was lower during night-time than during day-time in 11 out of 12 patients with prolonged postoperative ischemia. The sensitivity, specificity, and predictive values of negative and positive tests of the negative night-day difference of $\alpha 1$ for postoperative ischemia were 92%, 69%, 92% and 69% respectively. The area under ROC-curve c-index was 0.85, which indicates high sensitivity of the final logistic model.

The main finding in the study described above was that preoperatively increased nocturnal random heat rate dynamics (reduced short-term fractal exponent $\alpha 1$) had a predictive value for postoperative prolonged myocardial ischemia in patients with traumatic hip fracture.

The study carried out proved however also other findings, These other findings are described here by means of another study as follows.

Fifty-one patients were included in the HRV analysis before onset of ischemia, HRV indices were calculated for periods of 60–30 minutes and 30–0 minutes before onset of each ischemic episodes fulfilling the following criteria: 1) absence of any ischemic ST-segment changes during 90 minutes period preceding detected ischemic episode; 2) duration of single ischemic ST-segment change $\geq 1$ minute (to Include all ischemic episodes); 3) duration of single ischemic ST-segment change $\geq 10$ minutes (to include only prolonged ischemia). Three control periods were randomly selected for each patient. In patients with ischemia, the control periods were selected so that there were no ST-segment alteration 90 minutes before and 60 minutes after. In patients without ischemia, control periods were calculated for episodes during 60–30 minutes and 30–0 minutes before the reference points, similar to that done for the Ischemic episodes.

HRV of the segments of 30–0 minutes were compared with the segments of 60–30 minutes before prolonged ischemic episodes, and with the hole epoch of 24 hours within the prolonged ischemia group with Wilcoxon Test. Differences in HRV measures before onset of ischemia were tested with analysis of variance using linear mixed models, Three groups of beat segments were compared: segments before ischemic episodes, control segments of ischemic patients and control segments of non-ischemic patients. The correlation due to several measurements from the same patient was taken into account by defining the patient as a random factor in the linear model. The heart rate adjusted difference in $\alpha 1$ was also analysed by using heart rate as a covariant in the model.

Figure 2:
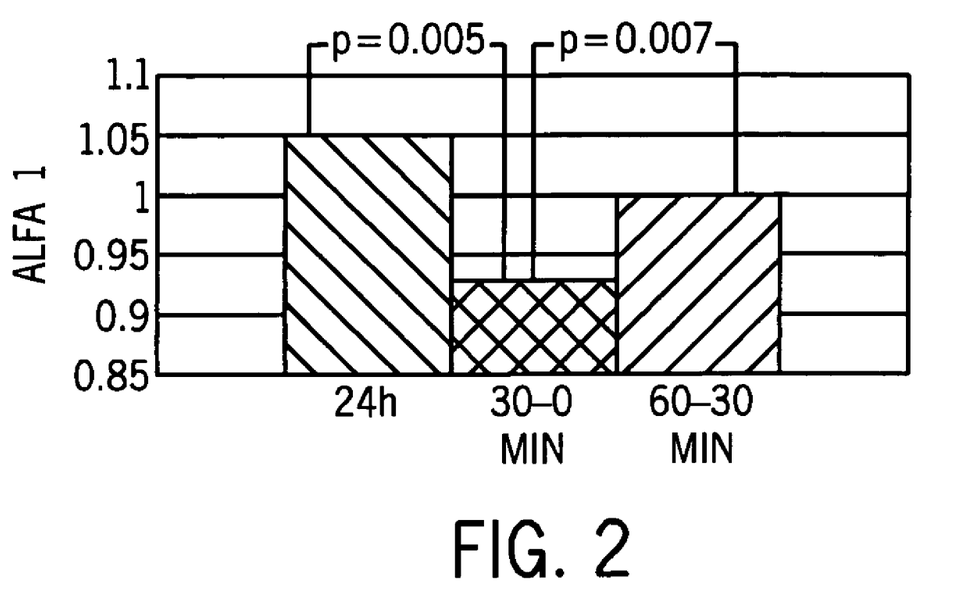
FIG. 2 shows variation of mean scaling exponent $\alpha 1$ and FIG. 3 shows variation of individual mean values of scaling exponent $\alpha 1$.
Figure 3:
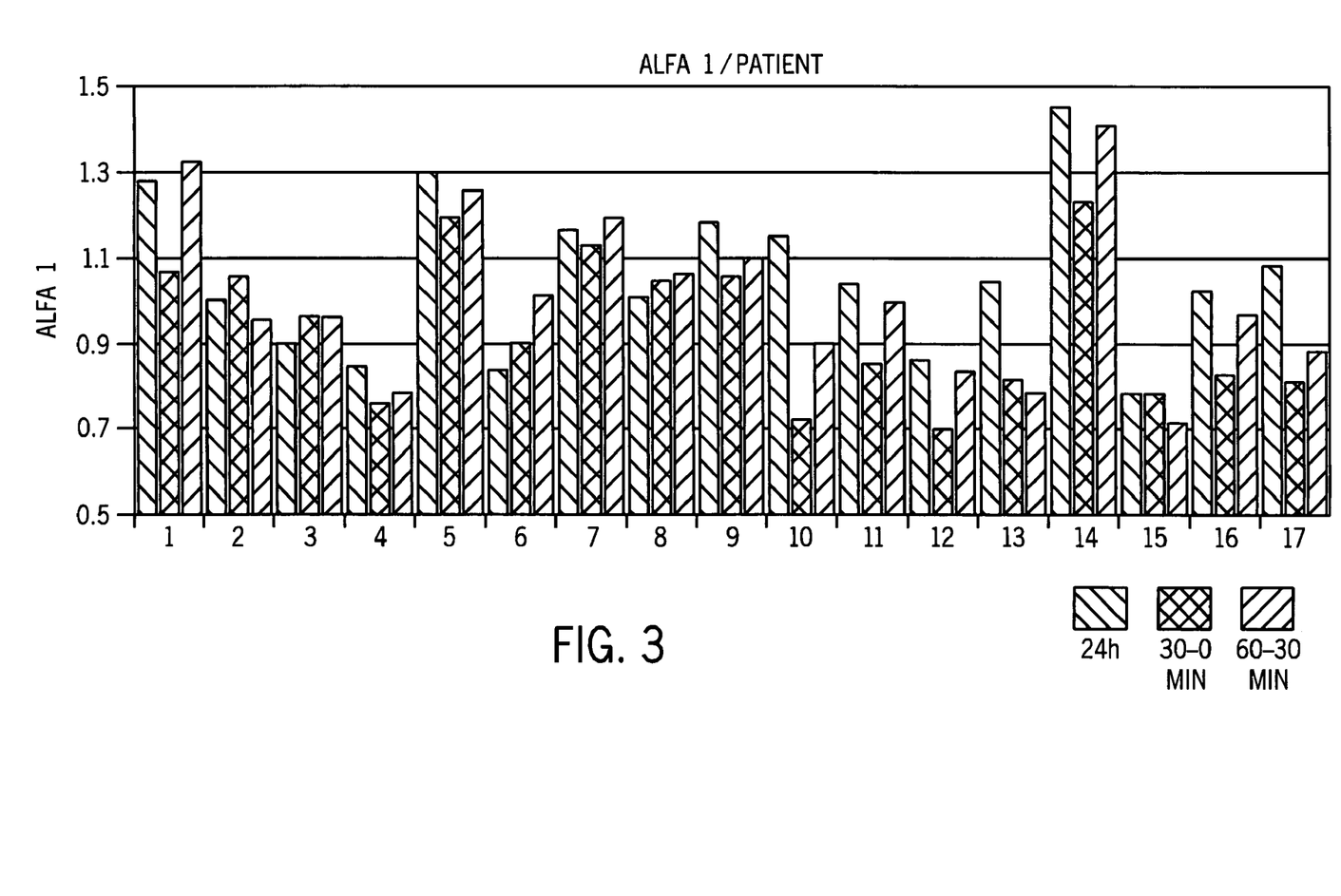

Of the 51 patients 17 had prolonged ischemic episodes, 7 only short ischemic episodes and 27 patients did not have ischemia. The scaling exponent $\alpha 1$ was significantly lower 30–0 minutes than 60–30 minutes before prolonged ischemic episodes (p<0.01). $\alpha 1$ of 30–0 minutes was also significantly lower than the mean value of 24 hours (p<0.01) (FIGS. 2 and 3). $\alpha 1$ of 30–0 minutes before prolonged ischemic episodes was significantly lower than the respective control periods in ischemic patients and in patients without ischemia (p<0.001 and p<0,05, respectively). A change of $\alpha 1$ (i.e. decrease) from 60–30 minutes to 30–0 minutes before prolonged ischemic episodes was significantly greater than before the respective control period in patients with and without ischemia (p<0.001 and p=0.01, respectively).

Scaling exponent $\alpha 1$ was for example also significantly lower before prolonged (>10 min) than short ($\geq 1$ min) ischemic episodes (p=0.03). Average heart rate did not show such difference between short and prolonged ischemic episodes. Scaling exponent $\alpha 1$ decreased in 76% and heart rate increased in 69% of the cases before onset of prolonged ischemic episodes. These findings are described in table 4. FIGS. 2 and 3 also describe said findings. FIG. 2 shows mean scaling exponent $\alpha 1$ of 24 h, 30–0 minutes and 60–30 minutes before prolonged ischemic episodes in 17 patients. Significance was tested with Wilcoxon pairs test. FIG. 3 shows individual mean values of scaling exponent $\alpha 1$ 24 h (left), 30–0 minutes (middle) and 60–30 minutes (right) before prolonged ischemic episodes.

The invention is by no means restricted to the embodiments described above, but the Invention can be varied totally freely within the scope of the claims. The invention can be used either in off-line systems or on-line systems, for example in on-line patient monitoring systems.

TABLE 1

| Patient characteristics. | | | |
| --- | --- | --- | --- |
| | No perioperative ischemia N = 16 | Perioperative ischemia N = 12 | P-value |
| Age [years] | 80 (7) | 78 (9) | 0.32 |
| Female/male | 14/2 | 10/2 | 1.00 |
| Body mass index [kg/m$^2$] | 26 (6) | 23 (3) | 0.10 |
| Previous myocardial infarction | 0 (0%) | 1 (8%) | 0.43 |
| Angina pectoris | 2 (12.5%) | 1 (8%) | 1.00 |
| Hypertension | 2 (12.5%) | 2 (17%) | 1.00 |

TABLE 1-continued

Patient characteristics.

|  | No perioperative ischemia N = 16 | Perioperative ischemia N = 12 | P-value |
|---|---|---|---|
| Patients with CAD or at least two risk factors for it* | 3 (19%) | 4 (33%) | 0.42 |
| Cardiac medications |  |  |  |
| Patients with β-blockers | 2 (12.5%) | 4 (33%) | 0.35 |
| ACE-inhibitors | 1 (6%) | 1 (8%) | 1.00 |
| Nitrates | 2 (12.5%) | 1 (8%) | 1.00 |

Abbreviations:
ACE: angiotensin-converting enzyme;
CAD: coronary artery disease.
Values are means (SD) or number (%) of patients. P-values are from Fisher's exact test except for age and body mass index which were tested with t-test.
*Risk factors for CAD: smoking, hypertension, diabetes, hypercholesterolemia[33]

TABLE 2

Statistics of 384 ischemic episodes in 12 patients with perioperative prolonged myocardial ischemia.

|  | Preoperative ischemia | Postoperative ischemia |
|---|---|---|
| Number of patients | 5/12 | 12/12 |
| Number of ischemic episodes | 51 | 333 |
| Duration of ischemia [min/episode] | 6.3 (1.4) [1.5–63] | 10.0 (1.4) [1.5–372] |
| AUC [mm · min/episode] | 6.9 (1.6) [1.4–72] | 13.5 (2.8) [1.4–806] |
| Duration of ischemia [min/patient] | 64.3 (23.4) [8–142] | 270.0 (73.0) [14–709] |
| AUC [mm · min/patient] | 70.3 (26.0) [9–157] | 372.0 (115) [17–1339] |

Abbreviations:
AUC: Area under the curve for ischemia.
Values are means (SEM) [range].

TABLE 3

Values of the heart rate variability measures in 28 patients with preoperative night and day Holter recordings.

| | No Ischemia N = 16 | | | | Prolonged postoperative ischemia N = 12 | | | |
|---|---|---|---|---|---|---|---|---|
| | 24-hour average | Night | Day | Night-day | 24-hour average | Night | Day | Night-day |
| Time domain | | | | | | | | |
| HR [beats/min] | 81 (2.2) | 80 (2.7) | 81 (2.6) | −0.7 (1.5) | 80 (2.1) | 78 (2.5) | 79 (2.0) | −1.6 (1.3) |
| SDNN [ms] | 28.9 (3.3) | 26.5 (3.0) | 31.4 (3.7) | −4.9 (2.4) | 32.6 (4.4) | 30.1 (4.8) | 32.6 (4.2) | −2.5 (2.9) |
| Frequency domain | | | | | | | | |
| VLF [ms$^2$] | 383 (109) | 309 (76) | 434 (145) | −124.7 (117.8) | 297 (63) | 271 (76) | 290 (54) | −19.1 (36.3) |
| LF [ms$^2$] | 179 (63) | 169 (71) | 172 (49) | −3.1 (41.7) | 278 (131) | 295 (131) | 216 (111) | 78.8 (58.1) |
| HF [ms$^2$] | 127 (34) | 96 (26) | 153 (47) | −57.0 (38.1) | 325 (176) | 338 (184) | 305 (166) | 33.2 (92.6) |
| DFA $\alpha_1$ | 1.02 (0.05) | 1.07 (0.04) | 0.99 (0.06) | 0.07 (0.04) | 1.02 (0.04) | 0.92 (0.08)† | 1.03 (0.06) | −0.11 (0.03)‡ |

Analyses were performed in 1000 beat segments.
Abbreviations:
DFA: Detrended fluctuation analysis;
HR: average heart rate;
SDNN: standard deviation of all RR intervals;
†P = 0.002 between night and day values within ischemia group (paired t-test).
‡P = 0.0018 association of the night-day difference with ischemia (logistic regression analysis).
Unmarked are non-significant.
Values are mean (SEM)

Scaling exponent-$\alpha_1$ was significantly lower before prolonged (>10 min) than short ($\geq$1 min) ischemic episodes (p=0.03). Average heart rate did not show such difference between short and prolonged ischemic episodes. Scaling exponent-$\alpha_1$ decreased in 76% and heart rate in 69% of the cases before onset of prolonged ischemic episodes.

TABLE 4

Scaling exponent $\alpha_1$ measures before onset of prolonged (>10 min) ischemic episodes in 17 patients.

| DFA $\alpha_1$ | Preischemic episodes n = 34 (A) | Control episodes of patients with ischemia n = 51 (B) | Control episodes of patients without ischemia n = 81 (C) | Overall difference between groups | A vs. B | A vs. C |
|---|---|---|---|---|---|---|
| 30–0 | 0.93(0.16) | 1.10 (0.25) | 1.06 (0.23) | <0.001 | <0.001 | 0.02 |
| Δ | −0.07(0.09) | 0.05 (0.015) | −0.008 (0.14) | <0.001 | <0.001 | 0.01 |

Analyses were performed in 1000 heat segments. Significance levels were tested with univariate logistic regression analysis.
Abbreviations:
DFA = detrended fluctuation analysis;
Δ = Change from 60–30 min to 30–0 min before onset of ischemia or before equivalent reference point
Values are means (SD).

The invention claimed is:

1. A method for predicting perioperative myocardial isehemia in a patient, the method comprising the steps of:
   obtaining heart rate data from the patient before an operation, the data being obtained in a preoperative time period including a nocturnal time period and a diurnal time period;
   carrying out a dynamic heart rate variability analysis of nocturnal heart rate data and of diurnal heart rate data to obtain a short term fractal correlation property of heart rate variability in a defined nocturnal time period and in a defined diurnal time period;
   comparing the defined nocturnal time period short term fractal correlation property and the defined diurnal time period short term fractal correlation property;
   determining from the comparison whether the nocturnal time period short term fractal correlation property is less than the diurnal time period short term fractal correlation property; and
   establishing a determination that the defined nocturnal time period short term fractal correlation property is less than the defined diurnal time period short term fractal correlation property as predictive for myocardial ischemia in a time subsequent to obtaining the heart rate data from the patient.

2. The method of claim 1 wherein the heart rate variability analysis is detrended fluctuation analysis (DFA).

3. The method of claim 2 wherein a scaling exponent α1 of the DFA is used as a short-term fractal correlation property.

4. The method of claim 1 or 2 wherein the analysis is on-line analysis.

5. The method of claim 2 wherein the heart rate data obtaining is initiated at least a day before the operation.

6. The method of claim 5 wherein the heart rate data obtained is ECG data obtained using Holter recording.

7. The method of claim 1 wherein the heart rate data obtaining is initiated at least a day before the operation.

8. The method of claim 7 wherein the heart rate data obtained is ECG data obtained using Holter recording.

9. A method for predicting perioperative myocardial ischemia in a patient, the method comprising the steps of:
   obtaining heart rate data perioperatively from the patient in a time period including a defined recent data acquisition time period and a defined data acquisition time period earlier than, and preceding, the defined recent data acquisition time period;
   carrying out a dynamic heart rate variability analysis of heart rate data from the recent time period and of heart rate data from the earlier time period to obtain a short term fractal correlation property of heart rate variability in a defined recent data acquisition time period and in a defined earlier data acquisition time period;
   comparing the defined recent data acquisition time period short term fractal correlation property and the defined earlier data acquisition time period short term fractal correlation property;
   determining from the comparison whether the recent data acquisition time period short term fractal correlation property is less than the earlier data acquisition time period short term fractal correlation property; and
   establishing a determination that the defined recent data acquisition time period short term fractal correlation property is less than the defined earlier data acquisition time period short term fractal correlation as predictive for myocardial ischemia in a time subsequent to obtaining the heart rate data from the patient.

10. The method of claim 9 wherein the heart rate variability analysis is detrended fluctuation analysis (DFA).

11. The method of claim 10 wherein a scaling exponent α1 of the DFA is used as a short-term fractal correlation property.

12. The method of claim 9 or 10 wherein the analysis is on-line analysis.

13. The method of claim 10 wherein the heart rate analysis of the acquired heart rate data is performed perioperatively.

14. The method of claim 13 wherein the heart rate data obtained is ECG data obtained using Holter recording.

15. The method of claim 9 wherein the heart rate analysis of the acquired heart rate data is performed perioperatively.

16. The method of claim 15 wherein the heart rate data obtained is ECG data obtained using Holter recording.

17. The method of claim 9 wherein the time periods used for comparison include at least two of; a recent data acquisition time period from 30–0 minutes prior to a recent point in time; an earlier data acquisition time period 60–30 minutes prior to the recent point in time; and an earlier 24 hour data acquisition time period.

18. An arrangement for predicting perioperative myocardial ischemia in a patient, the arrangement comprising:

means for obtaining heart rate data from the patient before an operation, the data being obtained in a preoperative time period including a nocturnal time period and a diurnal time period;

means receiving the obtained heart rate data for carrying out a dynamic heart rate variability analysis of nocturnal heart rate data and of diurnal heart rate data to obtain a short term fractal correlation property of heart rate variability in a defined nocturnal time period and in a defined diurnal time period;

means for comparing the defined nocturnal time period short term fractal correlation property and the defined diurnal time period short term fractal correlation property to determine from the comparison whether the nocturnal time period short term fractal correlation property is less than the diurnal time period short term fractal correlation property, and for establishing a determination that the nocturnal time period short term fractal correlation property is less than the diurnal time period short term fractal correlation property as a predictor for myocardial ischemia in a time subseciuent to obtaining the heart rate data from the patient.

19. The arrangement of claim 18 wherein the short term fractal analysis property is obtained from detrended fluctuation analysis (DFA).

20. The arrangement of claim 19 wherein a scaling exponent α1 of the DFA is used as a short-term fractal correlation property.

21. The arrangement of claim 18 or 19 wherein said means for carrying out dynamic heart rate variability analysis carries out on-line analysis.

22. The arrangement of claim 19 wherein said obtaining means initiates the heart rate data obtaining at least a day before the operation.

23. The arrangement of claim 22 wherein the heart rate data obtaining means is a Holter recorder obtaining ECG data.

24. The arrangement of claim 18 wherein said obtaining means initiates the heart rate data obtaining at least a day before the operation.

25. The arrangement of claim 24 wherein the heart rate data obtaining means is a Holter recorder for obtaining ECG data.

26. An arrangement for predicting perioperative myocardial ischemia in a patient, the arrangement comprising:

means for obtaining heart rate data perioperatively from the patient in a time period including a defined recent data acquisition time period and a defined data acquisition time period earlier than, and preceding, the recent data acquisition time period;

means receiving the obtained heart rate data for carrying out a dynamic heart rate variability analysis of heart rate data from the recent time period and heart rate data from the earlier data acquisition time period to obtain a short term fractal correlation property of heart rate variability in a defined recent data acquisition time period and in a defined earlier time period;

means for comparing the defined recent data acquisition time period short term fractal correlation property and the defined earlier data acquisition time period short term fractal correlation property to determine from the comparison whether the recent data acquisition time period short term fractal correlation property is less than the earlier data acquisition time period short term fractal correlation property, and for establishing a determination that the defined recent data acquisition time period short term fractal correlation property is less than the defined earlier data acquisition time period short term fractal correlation as a predictor for myocardial ischemia in a time subsequent to obtaining the heart rate data from the patient.

27. The arrangement of claim 26 wherein the short term fractal analysis property is obtained from detrended fluctuation analysis (DFA).

28. The arrangement of claim 27 wherein a scaling exponent α1 of the DFA is used as a short-term fractal correlation property.

29. The arrangement of claim 27 wherein said means for carrying out dynamic heart rate variability analysis carries out the analysis perioperatively.

30. The arrangement of claim 29 wherein the heart rate data obtaining means is a Holter recorder obtaining ECG data.

31. The arrangement of claim 26 wherein said means for carrying out dynamic heart rate variability analysis carries out the analysis perioperatively.

32. The arrangement of claim 31 wherein the heart rate data obtaining means is a Holter recorder for obtaining ECG data.

33. The arrangement of claim 26 wherein said means for carrying out dynamic heart rate variability analysis carries out on-line analysis.

34. The arrangement of claim 26 wherein said comparing means uses at least two of; a recent data acquisition time period from 30–0 minutes prior to the recent point in time; an earlier data acquisition time period 60–30 minutes prior to the recent point in time; and an earlier 24 hour data acquisition time period.

* * * * *